United States Patent
Fuerst et al.

(10) Patent No.: US 10,583,390 B2
(45) Date of Patent: Mar. 10, 2020

(54) CONTINUOUS PROCESS FOR CLEANING PROCESS WASTE AIR OBTAINED IN THE PRODUCTION OF SILICONES

(71) Applicant: Wacker Chemie AG, Munich (DE)

(72) Inventors: Josef Fuerst, Mehring (DE); Nils Becker, Burghausen (DE); Dieter Duschl, Burgkirchen (DE); Johann Schuster, Emmerting (DE)

(73) Assignee: WACKER CHEMIE AG, Munich (DE)

( * ) Notice: Subject to any disclaimer, the term of this patent is extended or adjusted under 35 U.S.C. 154(b) by 141 days.

(21) Appl. No.: 15/739,960

(22) PCT Filed: Jul. 11, 2016

(86) PCT No.: PCT/EP2016/066398
§ 371 (c)(1),
(2) Date: Dec. 26, 2017

(87) PCT Pub. No.: WO2017/009276
PCT Pub. Date: Jan. 19, 2017

(65) Prior Publication Data
US 2018/0369747 A1    Dec. 27, 2018

(30) Foreign Application Priority Data
Jul. 15, 2015   (DE) .................... 10 2015 213 252

(51) Int. Cl.
*B01D 53/22*     (2006.01)
*B01D 71/70*     (2006.01)
*B01D 71/78*     (2006.01)
*C07F 7/20*      (2006.01)
*B01D 53/00*     (2006.01)
*C08L 83/04*     (2006.01)

(52) U.S. Cl.
CPC ........... *B01D 53/226* (2013.01); *B01D 53/22* (2013.01); *B01D 53/228* (2013.01); *B01D 53/229* (2013.01); *B01D 71/70* (2013.01); *B01D 71/78* (2013.01); *C07F 7/20* (2013.01); *B01D 53/002* (2013.01); *B01D 2257/553* (2013.01); *B01D 2257/556* (2013.01); *C08L 83/04* (2013.01)

(58) Field of Classification Search
CPC .... B01D 53/22; B01D 53/226; B01D 53/228; B01D 53/229; B01D 71/70; B01D 2257/553; B01D 2257/556; C07F 7/20; C08L 83/04
See application file for complete search history.

(56) References Cited

U.S. PATENT DOCUMENTS

| 4,941,893 A | 7/1990 | Hsieh et al. |
| 6,221,131 B1 * | 4/2001 | Behling ............... B01D 53/228 95/50 |
| 2009/0277326 A1 * | 11/2009 | Baker .................... B01D 53/22 95/50 |
| 2014/0142205 A1 * | 5/2014 | Brinkmann ............. C01B 3/501 518/705 |

OTHER PUBLICATIONS

Ajhar, Marc et al., "Siloxane removal using silicone-rubber membranes", Separation and Purification Technology, 89, 2012, pp. 234-244. (Year: 2012).*
Ohlrogge, K. et al., "Membranes for Recovery of Volatile Organic Compounds", Comprehensive Membrane Science and Engineering, Enrico Drioli and Lidietta Girono, Editors, vol. 2, Academic Press, Elsevier, 2010, pp. 213-242. (Year: 2010).*
Marc Ajhar: "Membran-based Removal of Volatile Methylsiloxanes from Biogas" Thesis at the Hochschule Aachen (2011), pp. 68-104.
Ajhar M, Travesset M, Yüce S, Melin T: "Siloxane Removal From Landfill and Digester Gas—A Technology Overview", Bioresource Technology, Elsevier BV, GB, vol. 101, No. 9, May 1, 2010 (May 1, 2010), pp. 2913-2923, XP026870328, ISSN: 0960-8524.
J Patrick Montoya: "Membrane Gas Exchange Using Hollow Fiber Membranes to Separate Gases from Liquid and Gaseous Streams Types of Hollow Fiber Membranes", Jan. 1, 2010 (Jan. 1, 2010), XP055305659.
Marc Ajhar et al.: "Siloxane Removal Using Siliconerubber Membranes" Separation and Purification Technology, Elsevier Science, Amsterdam, NL, vol. 89, Jan. 3, 2012 (Jan. 3, 2012), pp. 234-244, XP028469169, ISSN: 1383-5866.
Ohlrogge K et al.: "Membranes for Recovery of Volatile Organic Compounds" Membrane Operations in Molecular Separations / [Contributors: G. Alberti . . . ] Comprehensive Membrane Science and Engineering / Drioli, Enrico ; vol. 2, Amsterdam [U.A.]: Elsevier, Acad. Press, 2010, NL, vol. 2, Jan. 1, 2010 (Jan. 1, 2010), pp. 213-242, XP008181852, ISBN: 978-0-444-53206-0.

* cited by examiner

Primary Examiner — Jason M Greene
(74) Attorney, Agent, or Firm — Brooks Kushman P.C.

(57) ABSTRACT

Organosilicon compounds in a process exhaust stream from silicone production are removed by contacting the exhaust stream with a semipermeable silicone membrane which is selectively permeable to organosilicon compounds and oxygen relative to nitrogen. The pressure on the permeate side of the membrane is preferably less than the pressure on the retentate side.

12 Claims, No Drawings

CONTINUOUS PROCESS FOR CLEANING PROCESS WASTE AIR OBTAINED IN THE PRODUCTION OF SILICONES

CROSS REFERENCE TO RELATED APPLICATIONS

This application is the U.S. National. Phase of PCT Appln. No. PCT/EP2016/066398 filed Jul. 11, 2016, which claims priority to German Application No. 10 2015 213 252.8 filed Jul. 15, 2015, the disclosures of which are incorporated in their entirety by reference herein.

BACKGROUND OF THE INVENTION

Field of the Invention

The process relates to a continuous process for purifying process exhaust air which contains organosilicon compounds and is obtained in the production process for preparing silicones.

Description of the Related Art

U.S. Pat. No. 4,941,893 discloses a process for removal gas in the preparation of semiconductor silicon metal, wherein hydrogen and hydrogen chloride are selectively separated off from chlorosilane in the gas mixture by means of a semipermeable membrane. As a selective membrane, preference is given to using a polysulfone composite membrane coated with sulfonated polysulfone.

M. Alkar, M. Travesset, S. Yüce and T. Melin, "Siloxan removal from landfill and digester gas—A technology overview", Bioresource Technology 101, 2913-2923 (2010), describes the separation of volatile siloxanes from landfill gas by means of various technologies, including by means of membranes.

In the thesis entitled "Membran-based Removal of Volatile Methylsiloxanes from Biogas" at the Hochschule Aachen (2011), pages 68-104 Marc Ajhar describes the use of a polydimethylsiloxane (PDMS) membrane for removing volatile methylsiloxanes from biogenic gases, with volatile methylsiloxanes present in small amounts in the region of about 0.15 g/m$^3$ being separated off from a methane/carbon dioxide gas mixture.

SUMMARY OF THE INVENTION

It was an object of the invention to provide a continuous process for purifying process exhaust air which contains organosilicon compounds and is formed in the production of silicones, in which organosilicon compounds, in particular siloxanes, can be selectively removed even in relatively large amounts from nitrogen/oxygen gas mixtures.

These and other objects are achieved by the inventdon, which employs a silicone separation membrane selectively permeable to organosilicon compounds and oxygen.

BRIEF DESCRIPTION OF THE DRAWINGS

FIG. 1 illustrates one embodiment of the invention.

DETAILED DESCRIPTION OF THE PREFERRED EMBODIMENTS

The invention thus provides a continuous process for purifying process exhaust air which contains organosilicon compounds and is obtained in the production process for preparing silicones, by separating organosilicon compounds selected from the group consisting of linear, cyclic and branched siloxanes having from 2 to 18 Si atams, triorganosilanols and mixtures thereof from the process exhaust air stream, containing nitrogen and oxygen by means of a membrane separation apparatus which contains a semipermeable membrane based on silicones, where the membrane is selectively permeable to organosilicon compounds and oxygen relative to nitrogen, and the feed gas stream which is to be separated and which contains organosilicon compounds, nitrogen and oxygen, is continuously introduced at the inlet of the membrane separation apparatus in which it is continuously separated by contacting with the membrane into a retentate gas substream which is depleted in organosilicon compounds and leaves the membrane separation apparatus, and a permeate gas substream which is enriched in organosilicon compounds and leaves the membrane separation apparatus.

The production process for preparing silicones is the preparation of silicone rubber, e.g. HTV, RTV and LSR silicone rubber, or the preparation of silicone polymers. The process exhaust air formed here contains organosilicon compounds selected from the group consisting of linear, cyclic and branched siloxanes having from 2 to 18 Si atoms, triorganosilanols and mixtures thereof.

This process exhaust air is conveyed as feed gas onto the semipermeable membrane according to the invention.

The organosilicon compounds present in the feed gas are preferably compounds selected from the group consisting of linear siloxanes of the formula $$R_3SiO(R_2SiO)_nSiR_3 \qquad (I)$$

where the radicals R are identical or different and are each a monovalent hydrocarbon radical having from 1 to 12 carbon atoms, preferably 1-6 carbon atoms, more preferably a methyl or vinyl radical, and n is 0 or an integer from 1 to 16,
cyclic siloxanes of the formula $$(R_2SiO)_x \qquad (II),$$

where R is as defined above and
x is an integer from 3 to 18, preferably from 3 to 6, triorganosilanols of the formula $$R_3SiOH \qquad (III)$$

where R is as defined above,
and mixtures thereof.

The key component of the exhaust gas purification according to the invention is a semipermeable membrane.

The process exhaust air stream obtained in the production of silicones is conveyed as a feed gas stream to the inlet of a membrane separation apparatus having a semipermeable membrane and is brought into contact with the membrane in the membrane separation apparatus. This membrane is preferably a polyoctylmethylsiloxane composite membrane, preferably a polyoctylmethylsiloxane composite membrane on a porous support structure composed of polyacrylonitrile/polyester nonwoven. (POMS). Such a membrane is obtainable from the Helmholtz-Zentrum Geesthacht, Zentrum für Material—und Küstenforschung GmbH, Max-Planck-Straße 1, 21502 Geesthacht, Germany.

The membrane material is able to dissolve organosilicon compounds present in the feed gas. A subatmospheric pressure is preferably applied by means of a vacuum pump on the permeate side of the membrane, i.e. on the side of the membrane which is opposite to that on which the feed gas is brought into contact with the membrane, so as to provide the driving force for migration of the compounds dissolved in the membrane material.

The feed gas preferably contains nitrogen in amounts of greater than or equal to 95% by volume and preferably contains oxygen in amounts of less than or equal to 5% by volume.

A subatmospheric pressure is applied on the permeate side of the membrane, preferably by means of a vacuum pump. The pressure in the permeate gas substream is preferably not more than 0.15 bar, which has the advantage that ignition of the organosilicon compounds separated, together with the oxygen, is prevented. Preference is given to a pressure of from 0.02 to 0.07 bar.

This pressure can preferably be achieved by means of liquid ring pumps. Significantly lower pressures can also be achieved by appropriate selection of the vacuum unit.

The pressure in the feed gas is preferably at least 1 bar and not more than 16 bar, with a pressure of from 1.0 to 1.5 bar being preferred.

The temperature in the feed gas and in the process of the invention is preferably not more than 100° C. and preferably at least 5° C., more preferably from 30° C. to 40° C.

The removal performance of the membrane can be varied via the pressure ratio of feed gas stream to permeate gas stream. Here, the pressures both on the feed side and on the permeate side can be selected appropriately. The pressure ratio of feed gas stream to permeate gas substream is preferably at least 7 and can be up to 16 million, with a pressure ratio of from 7 to 50 being preferred and a pressure ratio of from 15 to 20 being particularly preferred.

The resulting retentate gas stream is correspondingly depleted in organosilicon compounds. The retentate gas stream can either be continuously recirculated as inert gas to the process or be released continuously into the environment.

The retentate gas stream preferably contains a higher content of nitrogen and a lower content of oxygen than the feed gas stream. The retentate gas stream therefore preferably contains nitrogen in amounts of from 95 to 98% by volume and preferably contains oxygen in amounts of from 2 to 5% by volume.

The resulting permeate gas stream is correspondingly enriched in organosilicon compounds. These can be continuously condensed out from the permeate gas stream by corresponding measures, preferably by condensation, e.g. by condensation in a shell-and-tube heat exchanger or plate heat exchanger or a heat exchanger having a continuously cleanable surface, e.g. scratch coolers. The condensate obtained is preferably collected and utilized. The corresponding process exhaust gas stream can, depending on the configuration, be released continuously either together with the retentate gas stream or alone into the environment.

The membrane separation apparatus has a structure which enables the size of the active membrane area to be selected freely. As a result, a very large concentration range, in particular a large burden of volatile organosilicon compounds, in the feed gas, can be accommodated. This burden can range from a few ppm by weight up to a total of a number of kilograms/h.

The burden (g/h) of organosilicon compounds present in the feed gas is given by the product of volume flow ($m^3/h$) and concentration ($g/m^3$).

According to the thesis by Marc Ajhar, the concentrations of volatile methylsiloxanes in landfill gas are low, in particular less than 0.15 $g/m^3$ in total, and only small burdens of volatile methysiloxanes are removed from the landfill gas. In contrast thereto, according to the process of the invention high concentrations and burdens of organosilicon compounds are removed from the process exhaust air, i.e. the process exhaust air from industrial processes can be purified by means of the process of the invention.

The total concentration of the organosilicon compounds in the feed gas is preferably from 0.3 $g/m^3$ to 1000 $g/m^3$, preferably from 1 $g/m^3$ to 100 $g/m^3$.

The volume flow of the feed gas is preferably from 10 $m^3/h$ to 2000 $m^3/h$, preferably from 30 $m^3/h$ to 500 $m^3/h$, based on dry standard conditions (standard conditions: pressure of 1.01325 bar, temperature of 273.15 K and an absolute atmospheric humidity of 0%).

The burden (g/h) of organosilicon compounds present in the feed gas is preferably from 10 g/h to 10,000 g/h in total, more preferably from 1000 g/h to 5000 g/h in total.

This feed gas stream is, after contact with the membrane in the membrane separation apparatus, divided into a depleted retentate gas stream and an enriched permeate gas stream, with a process exhaust gas stream being obtained by separation of the organosilicon compounds from the permeate gas stream by means of suitable measures, e.g. condensation.

The burden (g/h), in each case based on each individual type of organosilicon compound or based on the sum of the organosilicon compounds in the feed gas, can be calculated from the product of volume flow ($m^3/h$) and concentration ($g/m^3$) of the feed gas.

Likewise, the burden (g/h) of organosilicon compounds in the retentate gas can be calculated from the measured volume flow (m³/h) and the measured concentration (g/m³) of the retentate gas. The permeability of the membrane with respect to the organosilicon compounds and thus the degree of depletion of the burden of organosilicon compounds in the retentate gas can then be determined as follows:

$$\eta[\%]=[1-(\text{Burden}_{Retentate}/\text{Burden}_{Feed})]\times 100$$

The permeability in respect of the organosilicon compounds is preferably from 30% to 100%, preferably from 50% to 100%, and more preferably from 60% to 90%.

The removal performance with respect to organosilicon compounds from the feed gases can be optimized even further by connecting a plurality of membrane separation apparatuses in series. Here, the remaining permeate gas stream is continuously fed to a further membrane separation apparatus connected in series. There, a renewed separation into permeate and retentate takes place.

The process is depicted by way of example in FIG. 1. The process exhaust air obtained in the production or silicones is fed as feed gas 1 to the inlet of a membrane separation apparatus having a semipermeable membrane 6. The feed gas is separated over the membrane 6 into a retentate gas 2 depleted in organosilicon compounds and a permeate gas 3 enriched in organosilicon compounds. The retentate gas 2 can either be recirculated as inert gas to the process or be discharged into the environment. On the permeate side of the membrane, a subatmospheric pressure which represents the driving force for migration of the compounds dissolved in the membrane material is preferably applied by means of a vacuum pump 7. The organosilicon compounds present in higher concentration in the permeate gas 3 can preferably be separated off by condensation by means of a condenser 8. The condensate 4 is preferably collected and utilized. The process exhaust gas 5 which arises is released either alone or together with the retentate gas into the environment.

Determination of the Volume Flow:

Differential pressure measurement using a Prandtl tube determined in accordance with DIN EN 15259.

Detection limit: 1 m³/s

Accuracy: ±10% (estimated)

Determination of the Organosilicon Compounds:

Integral sampling by means of an evacuated as collection vessel from exhaust gas stream via a capillary, qualitative and quantitative determination using GC-FID, by a method based on DIN EN 13464. Detection limit: <2 mg/m³ depending on the type of organosilicon compound Accuracy: ±10% (estimated)

Example 1

The process exhaust air formed continuously in the production of high-temperature-crosslinking silicone rubbers is fed as feed gas stream 1 at 50 m³/h to the membxane 6 at a temperature of 40° C. and a pressure of 1080 mbar absolute. This feed gas stream is separated at the membrane into 40 m³/h of retentate gas stream 2 and 10 m³/h of permeate gas stream 3. The pressure on the permeate side is 60 mbar absolute. This corresponds to a pressure ratio of 17.5. The condenser 8 was operated using a refrigerant at −10° C.

The concentrations of the important constituents of the process exhaust air, as indicated in table 1, were measured on qualified random samples. The corresponding burdens can be calculated therefrom with the aid of the measured volume flows. The feed gas stream 1 was taken off before entry into the membrane, the process exhaust gas 5 was measured downstream of the scratch cooler 8, and the retentate 2 was determined downstream of the membrane.

The results are summarized in table 1.

Feed Gas:

$N_2$: ≥95% by volume $O_2$: ≤5% by volume

Retentate:

$N_2$: 95-98% by volume $O_2$: 2-5% by volume

Organosilicon Compounds:

Si2: Hexamethyldisiloxane

M3SiOH: Trimethylsilanol

D3: Hexamethylcyclotrisiloxane

D4: Octmethylcyclotetrasiloxane

D5: Decamethylcyclopentasiloxane

D6: Undecamethylcyclohexasiloxane

TABLE 1

| Organosilicon comp. | Feed gas | | Process gas | | Retentate | | Permeability [%] |
|---|---|---|---|---|---|---|---|
| | Concentration [mg/m³] | Burden [mg/h] | Concentration [mg/m³] | Burden [mg/h] | Concentration [mg/m³] | Burden [mg/h] | |
| Si2 | 13,000 | 650,000 | 6800 | 68,000, | 2800 | 112,000 | 83 |
| M3SiOH | 8700 | 435,000 | 14,900 | 149,000 | 1900 | 76,000 | 83 |
| D3 | 680 | 34,000 | 1380 | 13,800 | 130 | 5200 | 85 |
| D4 | 300 | 15,000 | 300 | 3000 | 54 | 2160 | 86 |
| D5 | 140 | 7000 | 30 | 300 | 43 | 1720 | 75 |
| D6 | 30 | 1500 | 50 | 500 | 12 | 480 | 68 |
| Total | 22,850 | 1,142,500 | 23,460 | 234,600 | 4939 | 197,560 | 83 |

The permeability in respect of the organosilicon compounds is calculated as follows:

$$\eta[\%]=[1-(\text{Burden}_{Retentate}/\text{Burden}_{Feed})]\times 100 \text{ and}$$

Example 2

The process exhaust air formed continuously in the production of high-temperature-crosslinking silicone rubbers is fed as feed gas stream 1 at 50 m³/h to the membrane 6 at a temperature of 40° C. and a pressure of 1080 mbar absolute. This feed as stream is separated at the membrane into 40 m³/h of retentate 2 and 10 m³/h of permeate gas stream 3. The pressure on the permeate side is 60 mbar absolute. This corresponds to a pressure ratio of 17.5. The condenser 8 was operated using a refrigerant at −10° C.

The concentrations of the important constituents of the process exhaust air, as indicated in table 2, were measured on qualified random samples. The corresponding burdens can be calculated therefrom with the aid of the measured volume flows. The feed gas stream 1 was taken off before entry into the membrane, the process exhaust gas 5 was measured downstream of the scratch cooler 8, and the retentate 2 was determined downstream of the membrane.

The results are summarized in table 2.

Feed Gas:
$N_2$: ≥95% by volume
$O_2$: ≤5% by volume
Retentate:
$N_2$: 95-98% by volume
$O_2$: 2-5% by volume
Organosilicon Compounds: see Example 1 which it is continuously separated by the membrane into a retentate gas substream which is depleted in organosilicon compounds and leaves the membrane separation apparatus, and a permeate gas substream which is enriched in organosilicon compounds and leaves the membrane separation apparatus, wherein the initial total concentration of the organosilicon compounds in the process exhaust gas stream is from 0.3 g/m³ to 1000 g/m³, and the burden of the organosilicon compounds in the process exhaust gas stream is from 10 g/h to 10 000 g/h.

2. The process of claim 1, wherein the organosilicon compounds are compounds comprising linear siloxanes of the formula $$R_3SiO(R_2SiO)_nSiR_3 \quad (I),$$

where the radicals R are identical or different and are each a monovalent hydrocarbon radical having from 1 to 12 carbon atoms, and
n is 0 or an integer from 1 to 16,
cyclic siloxanes of the formula $$(R_2SiO)_x \quad (II),$$

where R is as defined above and
x is an integer from 3 to 18,
triorganosilanols of the formula $$R_3SiOH \quad (III),$$

where R is as defined above,
and mixtures thereof.

3. The process of claim 2, wherein in formulae (I), (II), and (III), the R radicals contain from 1 to 6 carbon atoms, and in formula (II), if present, x is an integer from 3 to 6.

TABLE 2

| Organosilicon comp. | Feed gas | | Process gas | | Retentate | | |
|---|---|---|---|---|---|---|---|
| | Concentration [mg/m³] | Burden [mg/h] | Concentration [mg/m³] | Burden [mg/h] | Concentration [mg/m³] | Burden [mg/h] | Permeability [%] |
| Si2 | 750 | 37,500 | 1000 | 10,000 | 300 | 12,000 | 68 |
| M3SiOH | 800 | 40,000 | 1400 | 14,000 | 300 | 12,000 | 70 |
| D3 | 750 | 37,500 | 800 | 8000 | 200 | 8000 | 79 |
| D4 | 300 | 15,000 | 600 | 6000 | 80 | 3200 | 79 |
| D5 | 200 | 10,000 | 400 | 4000 | 50 | 2000 | 80 |
| D6 | 50 | 2500 | 70 | 700 | 20 | 800 | 68 |
| Total | 2850 | 142,500 | 4270 | 42,700 | 950 | 38,000 | 73 |

The permeability in respect of the organosilicon compounds is calculated as follows:

$$\eta[\%]=[1-(\text{Burden}_{Retentate}/\text{Burdenc}_{Feed})]\times 100.$$

The invention claimed is:

1. A continuous process for purifying process exhaust gas containing organosilicon compounds, obtained in a production process for preparing silicones, comprising: separating linear, cyclic and branched siloxanes having from 2 to 18 Si atoms, triorganosilanols, and mixtures thereof from a process exhaust gas stream containing nitrogen and oxygen, by contacting the process exhaust gas stream with one or more membrane separation apparatuses which contain a polyoctylmethylsiloxane composite membrane as a semipermeable membrane, where the semipermeable membrane is selectively permeable to organosilicon compounds and oxygen relative to nitrogen, and the process exhaust gas stream which is to be separated and which contains organosilicon compounds, nitrogen, and oxygen is continuously introduced at an inlet of the membrane separation apparatus in 4. The process of claim 2, wherein R is methyl or vinyl.

5. The process of claim 1, wherein the pressure in the permeate gas substream is not more than 0.15 bar.

6. The process of claim 1, wherein the pressure ratio of the feed gas stream to permeate gas substream is in the range of from 7 to 50.

7. The process of claim 1, wherein the pressure ratio of the feed gas stream to permeate gas substream is in the range of from 15 to 20.

8. The process of claim 1, wherein the semipermeable membrane comprises a polyoctylmethylsiloxane (POMS) composite membrane on a porous support structure composed of polyacrylonitrile/polyester nonwoven.

9. The process of claim 1, wherein the retentate gas substream is continuously recirculated to the production process for preparing silicones.

10. The process of claim 1, wherein the retentate gas substream is continuously discharged into the environment.

11. The process of claim 1, wherein the organosilicon compounds present in higher concentration in the permeate gas substream are continuously separated from the permeate gas substream by condensation and the resulting purified permeate gas stream is continuously discharged into the environment.

12. The process of claim 1, wherein a plurality of membrane separation apparatuses are connected in series.

\* \* \* \* \*